(12) United States Patent
Stallings

(10) Patent No.: US 6,814,086 B2
(45) Date of Patent: Nov. 9, 2004

(54) ORTHODONTIC FLOSSING GUIDE

(75) Inventor: Joann Marie Stallings, Virginia Beach, VA (US)

(73) Assignee: Sturdy Floss, Inc., Virginia Beach, VA (US)

( * ) Notice: Subject to any disclaimer, the term of this patent is extended or adjusted under 35 U.S.C. 154(b) by 16 days.

(21) Appl. No.: 10/208,827

(22) Filed: Aug. 1, 2002

(65) Prior Publication Data

US 2004/0023181 A1 Feb. 5, 2004

(51) Int. Cl.$^7$ .............................................. A61C 15/00
(52) U.S. Cl. ...................................... 132/321; 433/141
(58) Field of Search ...................... 433/3, 141; 132/321, 132/329; 606/224; 223/102

(56) References Cited

U.S. PATENT DOCUMENTS

| | | | | |
|---|---|---|---|---|
| 2,522,794 A | * | 9/1950 | Medof | |
| 4,832,063 A | * | 5/1989 | Smole | 132/329 |
| 5,050,625 A | | 9/1991 | Siekmann | 132/323 |
| 5,094,255 A | * | 3/1992 | Ringle | 132/321 |
| 5,289,836 A | | 3/1994 | Peng | 132/329 |
| 5,311,889 A | * | 5/1994 | Ringle et al. | 132/321 |
| 5,353,820 A | | 10/1994 | Suhonen et al. | 132/321 |
| 5,392,794 A | * | 2/1995 | Striebel | 132/324 |
| 5,560,377 A | | 10/1996 | Donovan | 132/321 |
| 5,718,251 A | | 2/1998 | Gray et al. | 132/321 |
| 6,102,051 A | * | 8/2000 | Neves | 132/321 |
| 6,644,323 B1 | * | 11/2003 | Clark | 132/321 |

* cited by examiner

*Primary Examiner*—Cary E. O'Connor
(74) *Attorney, Agent, or Firm*—Hunton & Williams LLP

(57) ABSTRACT

The invention provides a flossing device to remove debris, food, plaque, and bacteria from in between the proximal surfaces of teeth undergoing orthodontic treatment. In an embodiment of the invention, a dental flossing guide comprises a lead portion and floss filament attached thereto and extending therefrom. The lead portion comprises two wires mechanically entwined with the floss filament and a soft flexible coating, with a good portion of the floss filament extending long enough to be grabbed by two hands. The flossing guide features a small diameter to fit between the orthodontic wire and the front portion of the tooth. The soft coating and a curvilinear tip of the flossing guide protects the gingival tissue when inserted into a patient's mouth. The flossing guide is used on patients that are undergoing orthodontic treatment to promote a healthy oral cavity environment. The flossing guide is easy to use by all ages.

23 Claims, 4 Drawing Sheets

ORTHODONTIC FLOSSING GUIDE

BACKGROUND OF THE INVENTION

1. Field of Invention

The present invention relates to dental flossing, and more particularly, to a flossing guide for use in patients undergoing orthodontic treatment.

2. Description of Related Art

Dental floss is used to remove debris such as plaque, food particles, and bacteria from in between teeth and underneath the gingival sulcus. The floss is guided in between adjacent teeth and down underneath the gingival sulcus. As the floss returns out of the gingival sulcus, it sweeps out debris, thereby creating a healthy oral environment. Dental floss is one of the key tools in the prevention of interproximal decay and periodontitis. For many individuals, flossing can be very tedious while undergoing orthodontic treatment. Individuals undergoing orthodontic treatment typically have a bracket affixed to the front portion of the teeth and a wire that connects each tooth together. The wire that connects from one tooth to another generally prevents the floss from sliding in between the adjacent teeth. For orthodontic patients, the floss needs to be placed underneath the orthodontic wire and in front of the teeth to be able to floss the proximal surfaces of each tooth.

Conventional flossing aids or guides are typically made of flimsy materials that bend easily and are uncontrollable when wet. Particularly, conventional flossing aids can not be contoured into a stable form for reaching difficult areas in the mouth. Moreover, once wet from saliva, conventional flossing aids are difficult to grab and maintain control. In addition, flossing guides typically consist of at least two separate pieces, thereby making it difficult for some individuals to use because they have to operate two separate pieces to complete one task. Further, conventional flossing guides are typically difficult to control due to their long length and inability to reform the device in a set direction for accurate placement. Without having accurate placement and control, it is time consuming and difficult to floss while wearing orthodontic wiring.

U.S. Pat. No. 5,050,625, for example, discloses a threaded device formed of a tube that includes a handle portion and a blade-like portion with a dental floss detachably retained therein. One disadvantage of such a device is that it can be harmful to the gingival tissue and is not applicable for flossing between the clearance formed between the teeth and orthodontic appliance. Moreover, each cleaning location requires the device to be rethread.

U.S. Pat. No. 5,289,836 discloses a dental floss device to remove debris underneath orthodontic wiring. This device has a semi-spherical guidepost of uniform small diameter and flossing bonded thereto. The flossing guide has a fixed plastic leader portion that is not bendable in any direction but keeps its existing form. This flossing aid is not accessible in all areas of the oral cavity due the fact each individual orthodontic appliance has its own fixed configuration.

SUMMARY OF THE INVENTION

The present invention overcomes these and other deficiencies of the related art by providing a flossing guide that can be used easily and conveniently to floss underneath orthodontic wiring, without damage to the gingival tissue. The flossing guide removes debris such as food, plaque, and bacteria on the tooth and under the gingival sulcus. Consequently, use of such a flossing guide prevents an occurrence of proximal caries and periodontal disease during the duration of orthodontic treatment.

In an embodiment of the invention, a flossing guide comprises floss filament with one end attached to a lead portion, which is formable, rigid, and has a soft coating that protects gingival tissue. Preferably, the lead portion comprises a number of wires with the end of the floss filament mechanically entwined and attached thereto. The lead portion has a curvilinear tip and is relatively small in diameter to pass through the space between the tooth and the orthodontic wire without difficulty, thereby guiding a string of floss filament into proper place for flossing. The soft coating can be colored to enhance the appearance of the flossing guide. The flossing guide is of sufficient composition to allow for reforming to ease the insertion to all areas of the mouth and to not loose its shape or stability when wet from saliva.

An advantage of the invention is that the flossing guide forms a single unit. Therefore, a user does not have to purchase nor manipulate several different items to perform one task. Another advantage is that a user does not have to thread floss through a hole prior to use. Another advantage is that the invention can be re-contoured into numerous shapes based on the mouth shape, hand size, and flossing technique of a particular user. Another advantage is that the invention remains controllable when wet and is therefore, easy to grasp in a mouth containing saliva. Moreover, the invention is large enough in size that it is easy to handle, but small enough in size that it can fit between the orthodontic wire and the tooth. Moreover, the invention enables easy flossing of the proximal surfaces of each tooth without harming gingival tissue. Moreover, the invention is easy and safe to use by all ages.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE PREFERRED EMBODIMENTS

Figure 1:
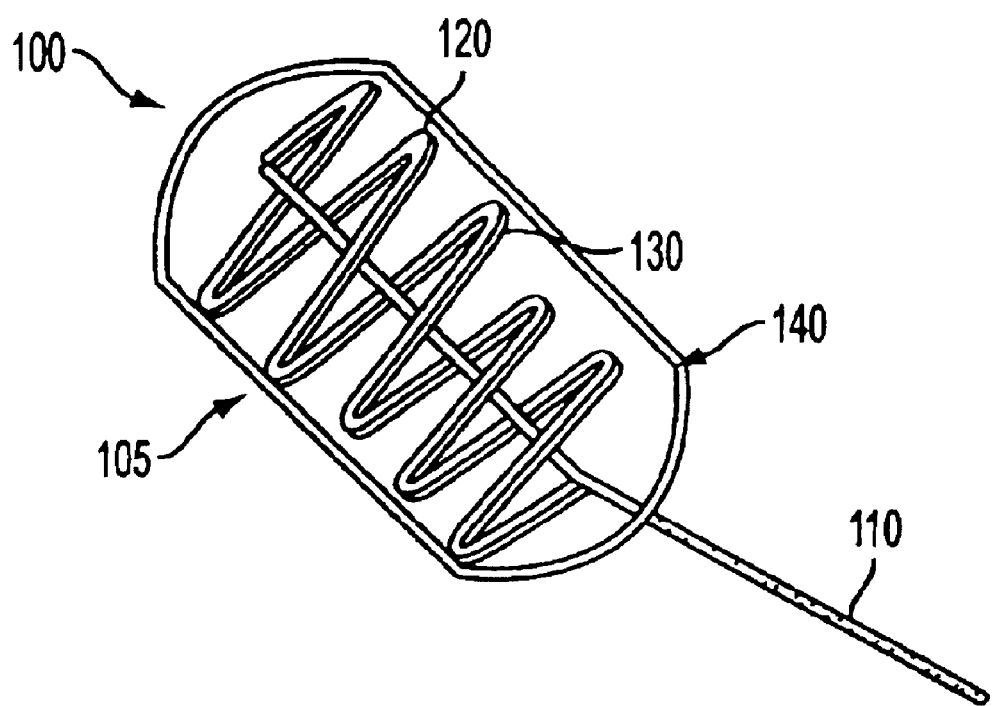
FIG. 1 illustrates a flossing guide according to an embodiment of the invention.

Preferred embodiments of the present invention and their advantages may be understood by referring to FIGS. 1–5B, wherein like reference numerals refer to like elements, and are described in the context of a flossing device for use during orthodontic treatment.

FIG. 1 illustrates a dental flossing guide 100 according to an embodiment of the invention. Particularly, dental flossing guide 100 comprises a lead portion 105 and a floss filament 110 attached thereto and extending therefrom. Lead portion 105 comprises a first flexible wire 120, a second flexible wire 130, and a coating 140. First flexible wire 120 and second flexible wire 130 are mechanically entwined or woven with floss filament 110 within lead portion 105. Coating 140 comprises a soft flexible material such as, but not limited to plastic, nylon, rubber, or a combination thereof. Floss filament 110 extends a length from the end of lead portion 105 long enough to be grasped by both hands to floss the proximal surface of each tooth. The front end of lead portion 105, i.e., the end opposite floss filament 110, features a curvilinear or dull tip for guiding underneath the orthodontic wire and in front of the teeth. The curvilinear or dull tip portion of dental flossing guide 100 protects the gingival tissue from damage during insertion of flossing guide 100 through the orthodontic wire. Floss filament 110 can be any type of conventional floss such as, but not limited to nylon (multifilament) and polytetrafluoroethylene (PTFE) (single filament) in waxed or unwaxed, and flavored or unflavored forms.

Floss 110 and wires 120 and 130 are attached together either by hand or machine in any fashion that would intertwine or interweave the components together, the implementation of which is apparent to one of ordinary skill in the art. In an embodiment of the invention, wires 120 and 130, and floss 110 are placed together in close proximity and then twisted together to form lead portion 105 of flossing guide 100. In related embodiments, one or more of the three components can be wrapped around the remaining components. After they are entwined or woven together, the lead portion 105 is coated with coating 140 in order to preferably cover wires 120 and 130 completely. Coating 140 only covers lead portion 105 leaving a floss extension long enough to floss easily and provides additional support to keep the wires and floss attached to each other. The wires and floss do not have to be entwined or woven together in any particular order.

Figure 2:
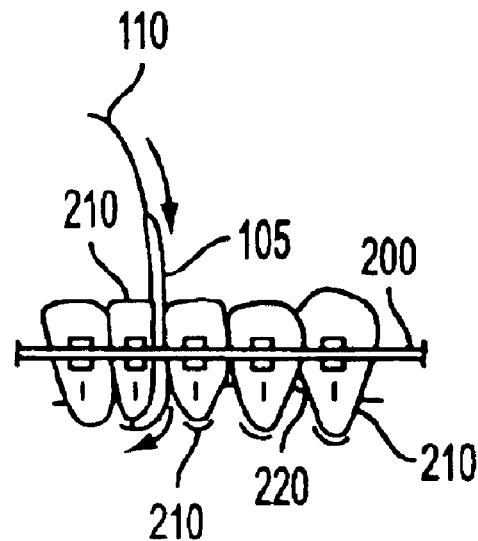
FIG. 2 illustrates the flossing guide of FIG. 1 placed in between orthodontic wire and teeth.
Figure 3:
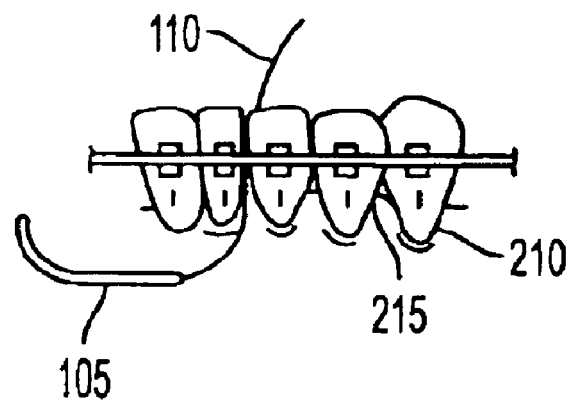
FIG. 3 illustrates the flossing guide of FIG. 1 in proper placement to floss proximal surfaces of teeth.

FIG. 2 illustrates dental flossing guide 100 placed in between orthodontic wire 200 and a user's teeth 210. Lead portion 105 of flossing guide 100 can be bent into a desirable shape and/or angle for insertion into a gap 220 between teeth 210 and the orthodontic wire 200. Preferably, lead portion 105 is of such a width that it easily fits into gap 220 and is flexible, but sturdy or rigid enough so that a user can easily grasp the flossing guide 100 when wet and in difficult areas of the mouth. Once lead portion 105 has been inserted through gap 220, as shown in FIG. 3, floss filament 110 is preferably long enough so the user can grasp to floss a proximal surface 215 of each tooth 210. Thus, enabling a user to floss between orthodontic wire 200 and teeth 210.

The flossing guide can be used for all areas of the mouth. In operation, a user decides where they are going to floss and then bends lead portion 105 to the desired shape before placing in the mouth. Once in the proper shape, the user places flossing guide 110 in the desired area and under orthodontic wire 200 and in front of teeth 210. Once it passes orthodontic wire 200, the user grabs the end and pulls lead portion 105 through to a point where only floss filament 110 is located between orthodontic wire 200 and teeth 210. Subsequently, the user grasps floss filament 110 on each side of orthodontic wire 200 and flosses proximal surface 215 of each tooth by moving floss filament 110 in between adjacent teeth and down underneath the gingival sulcus. Once the user is done with a particular area, they can remove flossing guide 100 from their mouth. Flossing guide 110 is then ready to be reshaped and placed into another area of the mouth for flossing.

Generally, flossing needs to be convenient and easy to accomplish for those who wear orthodontic appliances. The present invention integrates floss filament and a guide body into a single unit. The guide body comprises a nylon coating with two inner wires with floss mechanically attached to make one unit. The flossing guide is able to be reformed into a plurality of substantially rigid shapes for difficult areas to reach in the mouth, which may not be accessible with conventional flossing devices. Preferably, the flossing guide body is of such a size that it will fit between the orthodontic wire and the teeth but still large enough to comfortably grasp and maneuver in the mouth. The flossing guide has a curvilinear tip to protect the gingival tissue from harm. Accordingly, the flossing guide can be used by patients undergoing orthodontic treatment to help maintain oral health.

Figure 4:
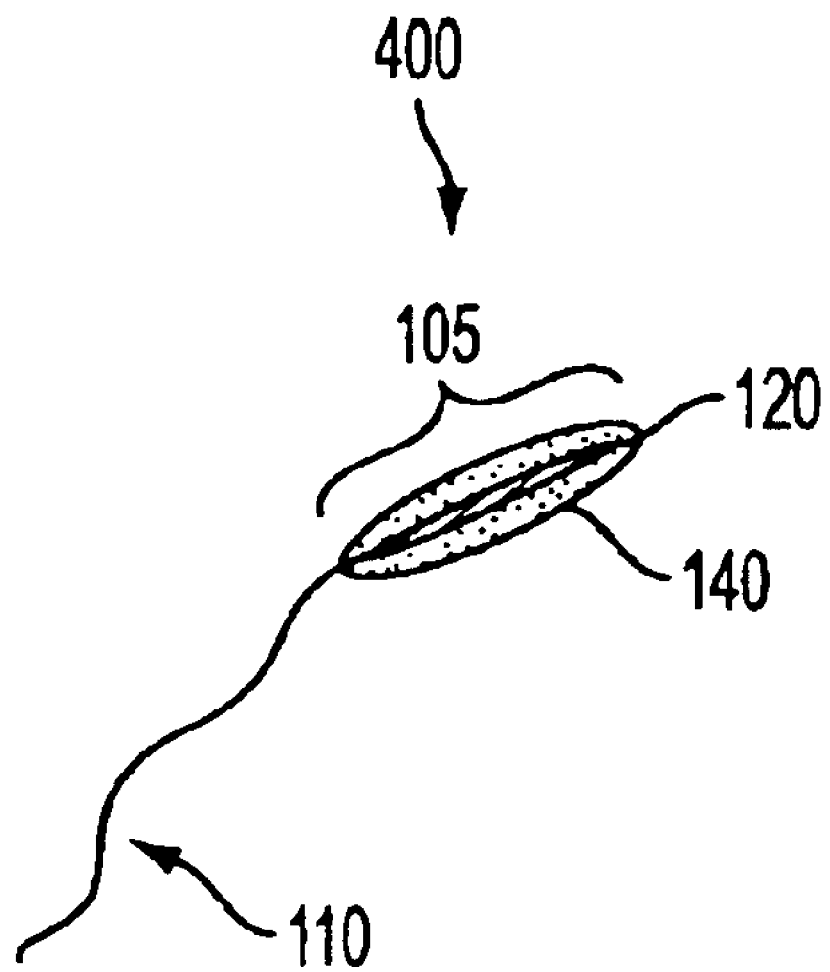
FIG. 4 illustrates a single wire flossing guide according to an embodiment of the invention.

Referring to FIG. 4, a dental flossing guide 400 comprises floss 110 and single wire 120 according to an embodiment of the invention. As shown, floss 110 is wrapped around wire 120 at lead portion 105. In a related embodiment, floss 110 and wire 120 can be entwined together. Coating 140 is applied to completely cover wire 120 and the portion of floss 110 wrapped around or entwined therewith. Flossing guide 400 is employed similar to that of guide 100 described above.

Figure 5A:
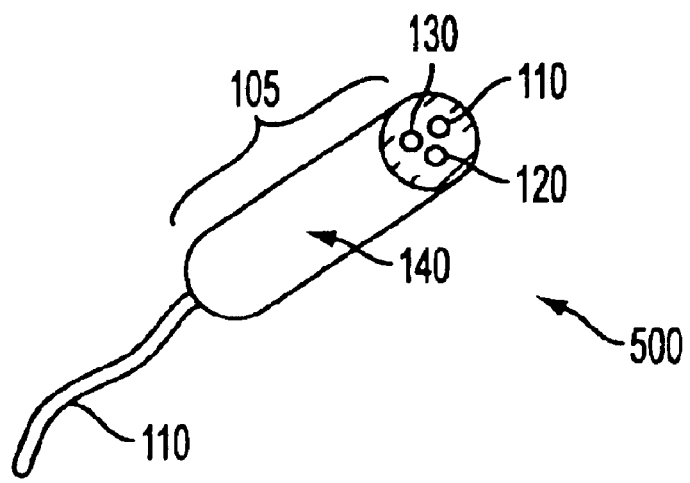
FIG. 5A and FIG. 5B illustrate a multiple wire flossing guide according to an embodiment of the invention.
Figure 5B:
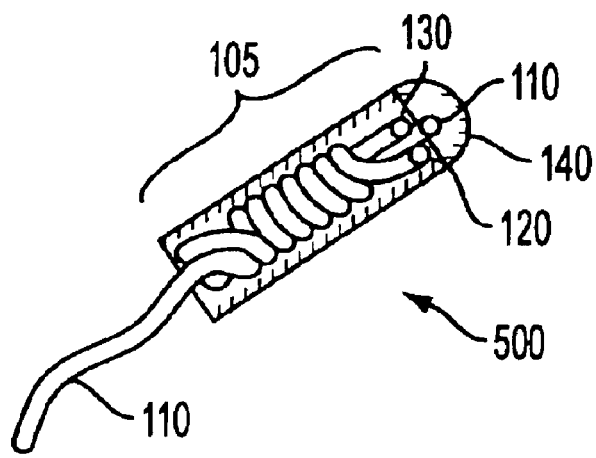

FIG. 5A illustrates a multiple wire flossing guide 500 according to an embodiment of the invention. Flossing guide 500 comprises floss 110, first wire 120, second wire 130, and a coating 140. In this figure, a cross-sectional view of a tip of lead portion 105 is illustrated to expose wires 120 and 130, and floss 110 within coating 140. Coating 140 is provided to cover wires 120 and 130, thereby preventing damage to gingival tissue during insertion of flossing guide 500 into a patient's mouth. Another cross-sectional view is shown in FIG. 5B to illustrate the intertwinement of floss 110 with wires 120 and 130. In a related embodiment of the invention, three or more wires can be used. In another related embodiment of the invention, one wire can be bent such that the wire comprises two portions (before and after the bend), which may be entwined with floss 110 in a similar manner as that of first and second wires 120 and 130 described above. For example, a single wire can be bent into a U-shape with substantially equal straight and parallel portions such that the portions take the place of wires 120 and 130. Preferably, the U-bend itself is placed at the tip of lead portion 105 and would serve to further prevent damage to gingival tissue. Flossing guide 500 is employed similar to that of guide 100 described above.

One of ordinary skill in the art recognizes that the dimensions of the components illustrated herein are not necessarily drawn to proper scale or actual size. Moreover, the dimensions of floss 110, wires 120 and 130, and coating 140 along with lead portion 105 can be varied as desired.

Other embodiments and uses of the invention will be apparent to those skilled in the art from consideration of the specification and practice of the invention disclosed herein. All references cited herein, including all U.S. patents, are hereby incorporated herein by reference in their entirety. Although the invention has been particularly shown and described with reference to several preferred embodiments thereof, it will be understood by those skilled in the art that various changes in form and details may be made therein without departing from the spirit and scope of the invention as defined in the appended claims.

I claim:

1. A flossing device comprising:
   a lead portion, wherein said lead portion comprises a curved tip, an end, a first wire and a soft flexible coating; and floss filament fixedly attached to said lead portion and extending from said end of said lead portion, wherein said soft flexible coating completely coats said wire and a portion of said floss filament.

2. The flossing device of claim 1, wherein said floss filament is entwined with said first wire.

3. The flossing device of claim 1, wherein said floss filament has a length suitable for flossing between teeth.

4. The flossing device of claim 1, wherein said soft flexible coating is selected from the group consisting of: nylon, rubber, plastic, or a combination thereof.

5. The flossing device of claim 1, wherein said soft flexible coating completely covers said first wire.

6. The flossing device of claim 5, wherein said first wire is flexible.

7. The flossing guide of claim 1, wherein said lead portion prevents damage to gingival tissue when reasonably inserted into a patient's mouth.

8. The flossing device of claim 1, wherein said end is opposite said curved tip.

9. The flossing device of claim 1, wherein said lead portion can be shaped to fit through a gap formed between orthodontic wire and teeth attached to said orthodontic wire.

10. A method for flossing teeth undergoing orthodontic treatment comprising the steps of:
   inserting the flossing device of claim 1 in a gap formed between an orthodontic wire and a tooth;
   pulling said flossing device through said gap; and
   flossing a proximal surface of said tooth with said floss filament.

11. The method of claim 10, further comprising the step of forming said lead portion into a shape suitable for insertion through said gap.

12. An orthodontic flossing device comprising:
   a string of dental floss,
   a first wire, and
   a coating, wherein said coating completely coats said first wire and a portion of said string of dental floss.

13. The device of claim 12 further comprising a second wire, wherein said coating completely coats said second wire.

14. The device of claim 13, wherein said first and second wires are intertwined with said string of dental floss.

15. The device of claim 12, wherein said string of dental floss is wrapped around or intertwined with said first wire.

16. The device of claim 12, wherein said string of dental floss comprises a material selected from the group consisting of: nylon, polytetrafluoroethylene, or a combination thereof.

17. The device of claim 12, wherein said first wire comprises a rigid, but flexible material.

18. The device of claim 12, wherein said coating comprises a soft material, which is not harmful to gingival tissue.

19. The flossing device of claim 18, wherein said soft flexible coating is selected from the group consisting of: nylon, rubber, plastic, or a combination thereof.

20. A flossing guide comprising:
   a lead portion, wherein said lead portion can be bent into a desired shape,
   a soft flexible coating covering a portion of said lead portion, and
   a floss filament fixedly attached to said lead portion, wherein said soft flexible coating also covers a portion of said floss filament.

21. The flossing device of claim 20, wherein said soft flexible coating is selected from the group consisting of: nylon, rubber, plastic, or a combination thereof.

22. The flossing device of claim 20, wherein said soft flexible coating completely covers said lead portion.

23. The flossing device of claim 20, wherein said lead portion comprises a curved tip.

* * * * *